(12) United States Patent
Schmidt

(10) Patent No.: US 10,224,136 B2
(45) Date of Patent: *Mar. 5, 2019

(54) DUAL DOUBLE HELIX CONDUCTORS USED IN AGRICULTURE

(71) Applicant: Medical Energetics Ltd., Galway (IE)

(72) Inventor: David G. Schmidt, Poway, CA (US)

(73) Assignee: Medical Energetics Ltd., Galway (IE)

( * ) Notice: Subject to any disclaimer, the term of this patent is extended or adjusted under 35 U.S.C. 154(b) by 276 days.

This patent is subject to a terminal disclaimer.

(21) Appl. No.: 15/164,539

(22) Filed: May 25, 2016

(65) Prior Publication Data

US 2016/0365186 A1 Dec. 15, 2016

Related U.S. Application Data

(60) Provisional application No. 62/230,540, filed on Jun. 9, 2015.

(51) Int. Cl.
| | |
|---|---|
| *H01F 7/06* | (2006.01) |
| *A01K 67/00* | (2006.01) |
| *H01F 27/28* | (2006.01) |
| *A01G 7/04* | (2006.01) |
| *A01G 22/00* | (2018.01) |
| *A01K 29/00* | (2006.01) |
| *A61N 1/40* | (2006.01) |
| *A61N 2/02* | (2006.01) |
| *H01F 5/00* | (2006.01) |

(52) U.S. Cl.
CPC .............. *H01F 7/064* (2013.01); *A01G 7/04* (2013.01); *A01G 22/00* (2018.02); *A01K 29/00* (2013.01); *A01K 67/00* (2013.01); *A61N 1/40* (2013.01); *A61N 2/02* (2013.01); *H01F 5/00* (2013.01); *H01F 27/2823* (2013.01)

(58) Field of Classification Search
CPC .......... A01G 22/00; A01G 1/001; A01G 7/04; A01K 67/00; A01K 29/00; H01F 7/064; H01F 27/28; H01F 5/00; H01F 27/2823; A61N 1/40; A61N 2/02
See application file for complete search history.

(56) References Cited

U.S. PATENT DOCUMENTS

| | | |
|---|---|---|
| 1,898,661 A | 2/1933 | Hagen |
| 2,035,274 A | 3/1936 | Mougey |
| 2,297,454 A | 9/1942 | Berger |
| 2,850,666 A | 9/1958 | Brewer |
| 3,037,175 A | 5/1962 | Ruthroff |
| 3,066,295 A | 11/1962 | Krause |
| 3,519,964 A | 7/1970 | Chorney |

(Continued)

FOREIGN PATENT DOCUMENTS

| | | |
|---|---|---|
| GB | 479841 A | 2/1938 |
| GB | 2480610 A | 11/2011 |

(Continued)

*Primary Examiner* — Christine H Matthews
*Assistant Examiner* — Joshua D Lannu
(74) *Attorney, Agent, or Firm* — ARC IP Law, PC; Joseph J. Mayo

(57) ABSTRACT

A system including one or more bodies having an underlying structure resembling a double helix may be arranged and used, to produce useful electromagnetic effects for various agricultural applications, including promotion of growth in organisms and organic matter.

30 Claims, 10 Drawing Sheets

(56) References Cited

U.S. PATENT DOCUMENTS

| | | |
|---|---|---|
| 3,588,689 A | 6/1971 | Crawford |
| 3,683,393 A | 8/1972 | Self |
| 3,760,812 A | 9/1973 | Timm |
| 3,774,452 A | 11/1973 | Tullos |
| 4,131,759 A | 12/1978 | Felkel |
| 4,229,676 A | 10/1980 | Manoly |
| 4,266,532 A | 5/1981 | Ryaby |
| 4,439,702 A | 3/1984 | Belikov |
| 4,489,276 A | 12/1984 | Yu |
| 4,832,051 A | 5/1989 | Jarvik |
| 4,989,617 A | 2/1991 | Memberg |
| 5,077,934 A | 1/1992 | Liboff |
| 5,079,458 A | 1/1992 | Schuster |
| 5,173,669 A | 12/1992 | Manoly |
| 5,182,537 A | 1/1993 | Thuis |
| 5,339,061 A | 8/1994 | Reick |
| 5,359,340 A | 10/1994 | Yokota |
| 5,366,493 A | 11/1994 | Scheiner |
| 5,464,456 A | 11/1995 | Kertz |
| 5,654,723 A | 8/1997 | Craven |
| 5,819,467 A | 10/1998 | Zucker |
| 5,851,206 A | 12/1998 | Guglielmi |
| 5,892,480 A | 4/1999 | Killen |
| 5,909,165 A | 6/1999 | Leupold |
| 5,954,630 A | 9/1999 | Masaki |
| 5,977,932 A | 11/1999 | Robinson |
| 6,005,462 A | 12/1999 | Myers |
| 6,169,523 B1 | 1/2001 | Ploussios |
| 6,239,760 B1 | 5/2001 | VanVoorhies |
| 6,300,920 B1 | 10/2001 | Pertl |
| 6,520,986 B2 | 2/2003 | Martin |
| 6,552,530 B1 | 4/2003 | Vaiser |
| 6,770,023 B2 | 8/2004 | Vaiser |
| 6,921,042 B1 | 7/2005 | Goodzeit |
| 6,978,179 B1 | 12/2005 | Flagg |
| 7,148,783 B2 | 12/2006 | Parsche |
| 7,154,368 B2 | 12/2006 | Sweeney |
| 7,375,449 B2 | 5/2008 | Butterfield |
| 8,323,328 B2 | 12/2012 | Martin |
| 8,463,407 B2 | 6/2013 | Bulkes |
| 8,652,023 B2 | 2/2014 | Schmidt |
| 8,653,925 B2 | 2/2014 | Schmidt |
| 8,749,333 B2 | 6/2014 | Schmidt |
| 8,919,035 B2 | 12/2014 | Schmidt |
| 8,961,384 B2 | 2/2015 | Schmidt |
| 9,030,283 B2 | 5/2015 | Schmidt |
| 9,370,667 B2 | 6/2016 | Schmidt |
| 9,406,421 B2 | 8/2016 | Schmidt |
| 9,504,845 B2 | 11/2016 | Schmidt |
| 2003/0011527 A1 | 1/2003 | Kokorin |
| 2003/0095022 A1 | 5/2003 | Boynton et al. |
| 2003/0158585 A1 | 8/2003 | Burnett |
| 2003/0169132 A1 | 9/2003 | Vaiser |
| 2003/0230427 A1 | 12/2003 | Gareis |
| 2005/0094989 A1 | 5/2005 | Halpin |
| 2005/0121396 A1 | 6/2005 | Kosakewich |
| 2005/0228209 A1 | 10/2005 | Schneider et al. |
| 2007/0024520 A1 | 2/2007 | Preble |
| 2007/0258329 A1 | 11/2007 | Winey |
| 2008/0161884 A1 | 7/2008 | Chandler |
| 2008/0266203 A1 | 10/2008 | Rossetto |
| 2009/0083969 A1 | 4/2009 | Meinke |
| 2009/0206974 A1 | 8/2009 | Meinke |
| 2009/0260849 A1 | 10/2009 | Cardas |
| 2010/0005711 A1 | 1/2010 | McNeff |
| 2010/0057655 A1 | 3/2010 | Jacobson |
| 2010/0113862 A1 | 5/2010 | Kotowich |
| 2010/0114280 A1 | 5/2010 | Hill |
| 2010/0121131 A1 | 5/2010 | Mathes |
| 2010/0152811 A1 | 6/2010 | Flaherty |
| 2010/0179630 A1 | 7/2010 | Williams |
| 2012/0101366 A1 | 4/2012 | Ruohonen |
| 2012/0143285 A1 | 6/2012 | Wang |
| 2012/0223800 A1 | 9/2012 | Schmidt |
| 2013/0192129 A1 | 8/2013 | Schmidt |
| 2013/0211181 A1* | 8/2013 | Schmidt ............... A61N 2/008 600/13 |
| 2013/0274542 A1 | 10/2013 | Volo et al. |
| 2013/0285782 A1 | 10/2013 | Schmidt |
| 2014/0097925 A1 | 4/2014 | Schmidt |
| 2014/0100412 A1 | 4/2014 | Schmidt |
| 2014/0218149 A1 | 8/2014 | Schmidt |
| 2014/0371514 A1 | 12/2014 | Schmidt |
| 2015/0119630 A1 | 4/2015 | Schmidt |
| 2015/0119631 A1 | 4/2015 | Schmidt |
| 2015/0119632 A1 | 4/2015 | Schmidt |
| 2015/0157871 A1 | 6/2015 | Schmidt |
| 2015/0283393 A1 | 10/2015 | Schmidt |
| 2015/0283394 A1 | 10/2015 | Schmidt |
| 2016/0172088 A1 | 6/2016 | Schmidt |
| 2016/0172101 A1 | 6/2016 | Schmidt |
| 2016/0247614 A1 | 8/2016 | Schmidt |
| 2016/0247617 A1 | 8/2016 | Schmidt |

FOREIGN PATENT DOCUMENTS

| | | |
|---|---|---|
| WO | 2012118971 A2 | 9/2012 |
| WO | 2013112810 A1 | 8/2013 |
| WO | 2013123009 A1 | 8/2013 |

* cited by examiner

DUAL DOUBLE HELIX CONDUCTORS USED IN AGRICULTURE

FIELD OF THE INVENTION

The invention relates to bodies that include helically wound runners around which conductive wires are wound, devices including such bodies, (electrical) systems including such bodies, and/or (agricultural) applications using such bodies. As used herein, the term "agriculture" refers to the cultivation of animals, plants, fungi, and other life forms for food, fiber, bio-fuel, medicinal products and other products used to sustain and/or enhance human life. This cultivation may be referred to as agricultural application.

A body with one or more runners may be referred to as a coil. Devices and systems may include one or more coils, e.g. in specific and predetermined arrangements. The invention further relates to the manufacture of such bodies, devices, and/or systems. The invention further relates to methods of operation of such devices and systems, and applications thereof. The invention further relates to such devices and/or systems configured to promote growth in organisms and organic matter by using electromagnetic effects such as electromagnetic fields.

BACKGROUND OF THE INVENTION

It is known that spirally wound electrical conductors may exhibit certain electromagnetic properties and/or electromagnetic effects. For example, it is known that an electromagnetic coil may act as an inductor and/or part of a transformer, and has many established useful applications in electrical circuits. Multiple coils may be used to exploit an electromagnetic field and/or other electromagnetic effects that are created when, e.g., one or more active current sources are operatively coupled to the coils.

SUMMARY

One aspect of the invention relates to a system comprising one or more bodies, one or more current sources, one or more sources of electromagnetic radiation, one or more conductive wires, and/or other components. Individual bodies may include two or more intertwined helically wound runners. A first runner may be coupled to the second runner by struts and/or held in position through other support structures. Individual runners may have a helical shape. Individual bodies may be arranged in toroidal shapes. One or more conductive wires may be spirally wound around at least one runner.

Specific alternating currents may be supplied to the conductive wires. In some implementations, conductive wires for each individual body may be supplied with a high-frequency carrier wave that is modulated with an acoustic signal. In some implementations, different acoustic signals may be used for different bodies in the system.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION

Figure 1:
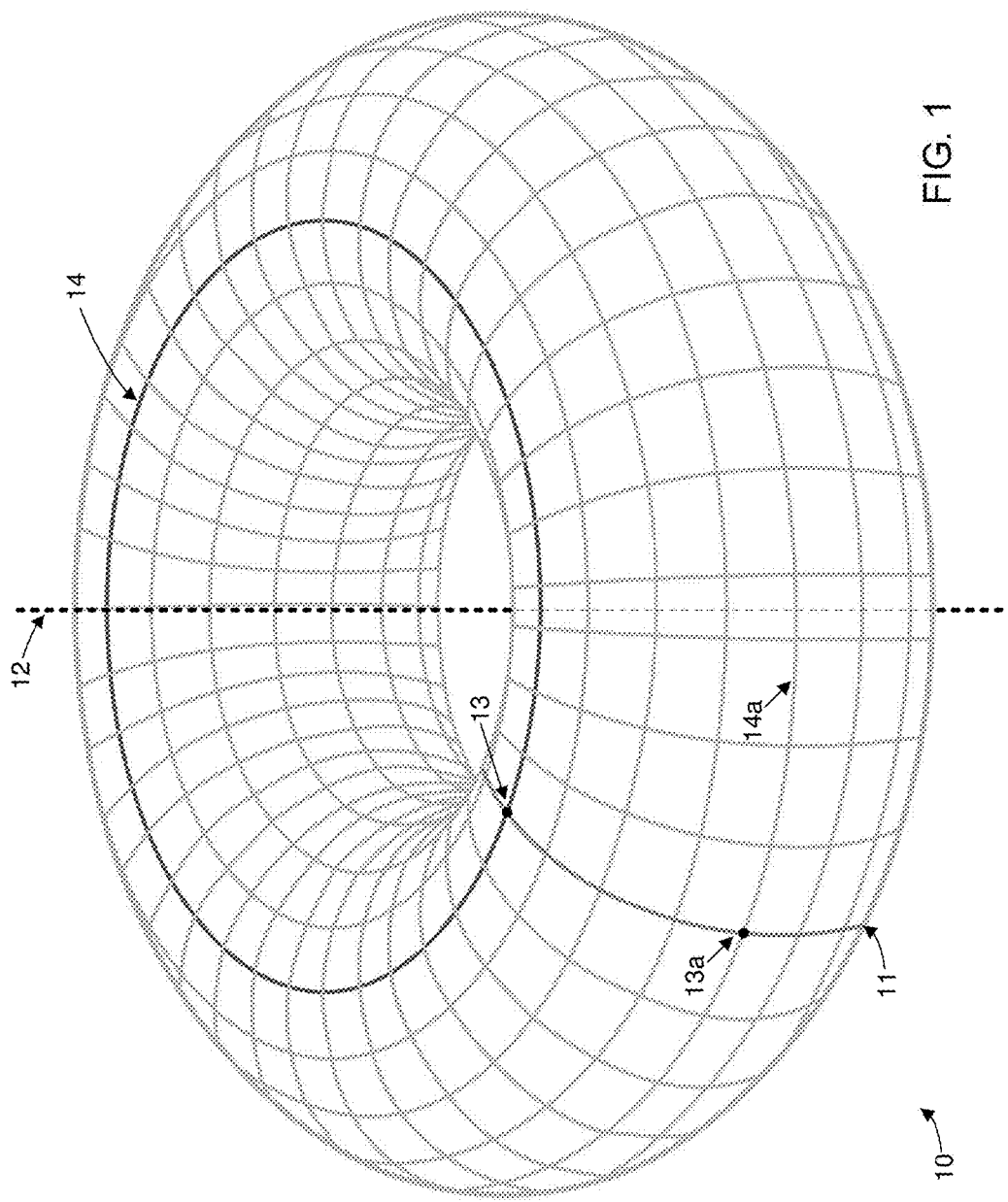
FIG. 1 illustrates a toroidal shape.

FIG. 1 illustrates a toroidal shape 10. A toroidal shape such as shape 10 may be formed by revolving a circle 11 (partially shown in FIG. 1) in three-dimensional space about an axis 12 that is coplanar with circle 11. Toroidal shape 10 may be informally referred to as a donut shape or a bagel shape. Axis 12 may be said to go through the donut hole of toroidal shape 10. The surface of toroidal shape 10 may be a torus. Circle 11 may include a point 13, a point 13a, and other points. As circle 11 is revolved to form toroidal shape 10, point 13 describes a circle 14 that defines a plane. This plane is perpendicular to axis 12. Different points on circle 11 describe different circles on the surface of toroidal shape 10. As circle 11 is revolved, point 13a describes a circle 14a that defines a plane. This plane bisects toroidal shape 10 and is perpendicular to axis 12. In some implementations, for a particular point 13a and a particular circle 14a, the defined plane bisects toroidal shape 10 into two similar, congruent, circular, and/or isometric halves, e.g. as if cutting a bagel in half such that the surface area of the cut has the shape of a mathematical ring or annulus (i.e. a first circle with a relatively smaller radius completely inside a second circle with a relatively larger radius, with both circles being concentric, the term "relatively" being used to relate the first circle and the second circle).

Figure 2:
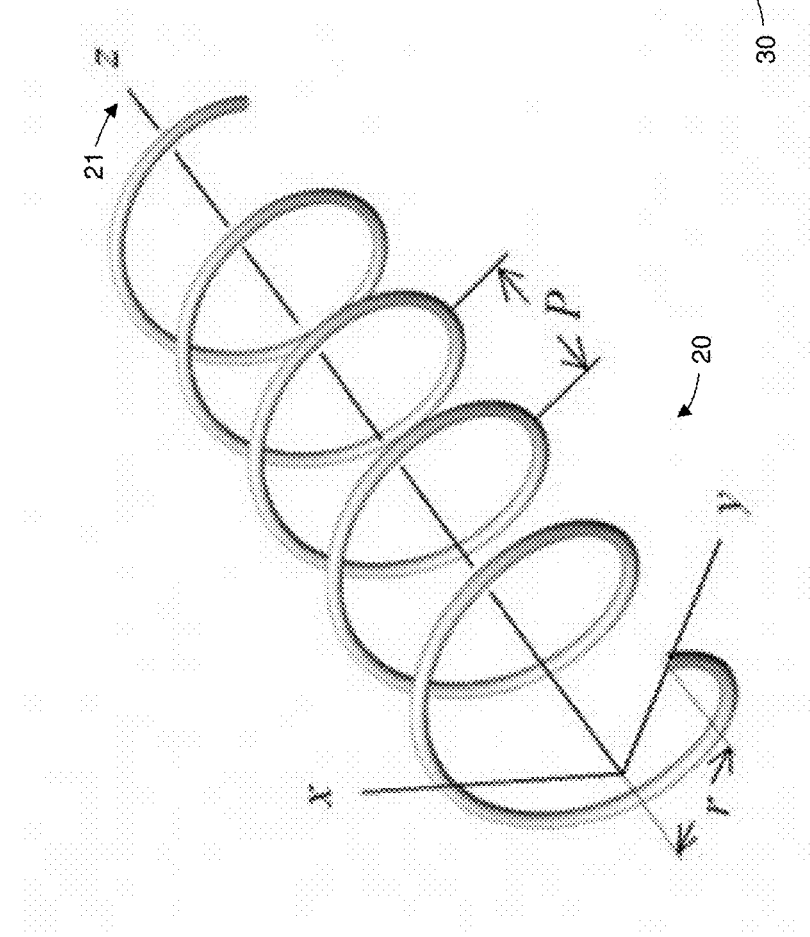
FIG. 2 illustrates a helical shape.

FIG. 2 illustrates a helical shape 20. A helical shape such as shape 20 may be formed by a curve in three-dimensional space that has the property that the tangent line at any point makes a constant angle with a fixed line called an axis 21 (labeled "z" in FIG. 2, and perpendicular to both the "x" and "y" axes in FIG. 2). The width of one complete helix turn or revolution, measured parallel to axis 21, is called pitch (labeled "P" in FIG. 2). The shortest distance from helical shape 20 to axis 21 is called the radius (labeled "r" in FIG. 2). Helical shape 20 may have a constant radius, and be referred to as a circular helix. Note that in some embodiments, an axis similar to axis 21 may be curved instead of being straight, as depicted in FIG. 2.

Figure 3:
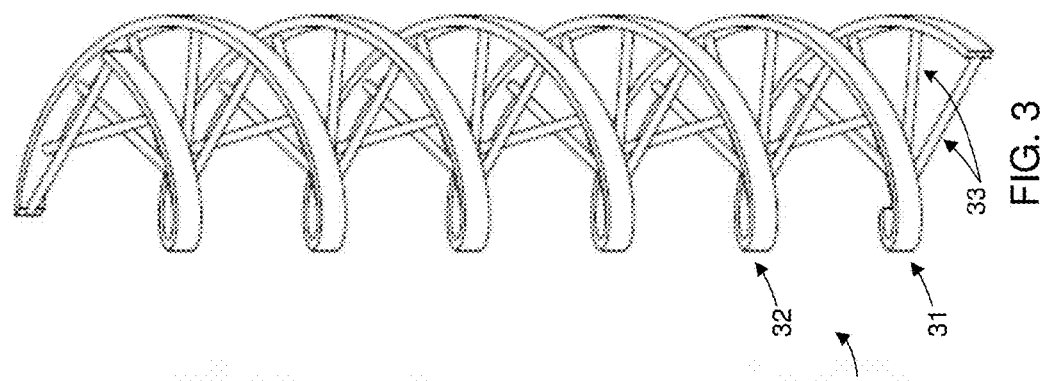
FIG. 3 illustrates an exemplary body including two intertwined helically wound runners in the shape of a double helix, the runners being coupled and/or supported by struts.

FIG. 3 illustrates an exemplary body 30 including two intertwined helically wound runners, a first runner 31 and a second runner 32, in the shape of a double helix, the runners being coupled and/or supported by struts 33. In some implementations, the runners of a double helix may be supported by other support structures. The double helix may include two helical shapes, each of which may be similar to helical shape 20 as shown in FIG. 2. It is noted that the shape of body 30 resembles the general shape of deoxyribonucleic acid (DNA), e.g. a double helix. A helical shape may have a straight axis, as shown in FIG. 2 and FIG. 3, or a curved axis as shown in, e.g., FIG. 4.

Figure 4:
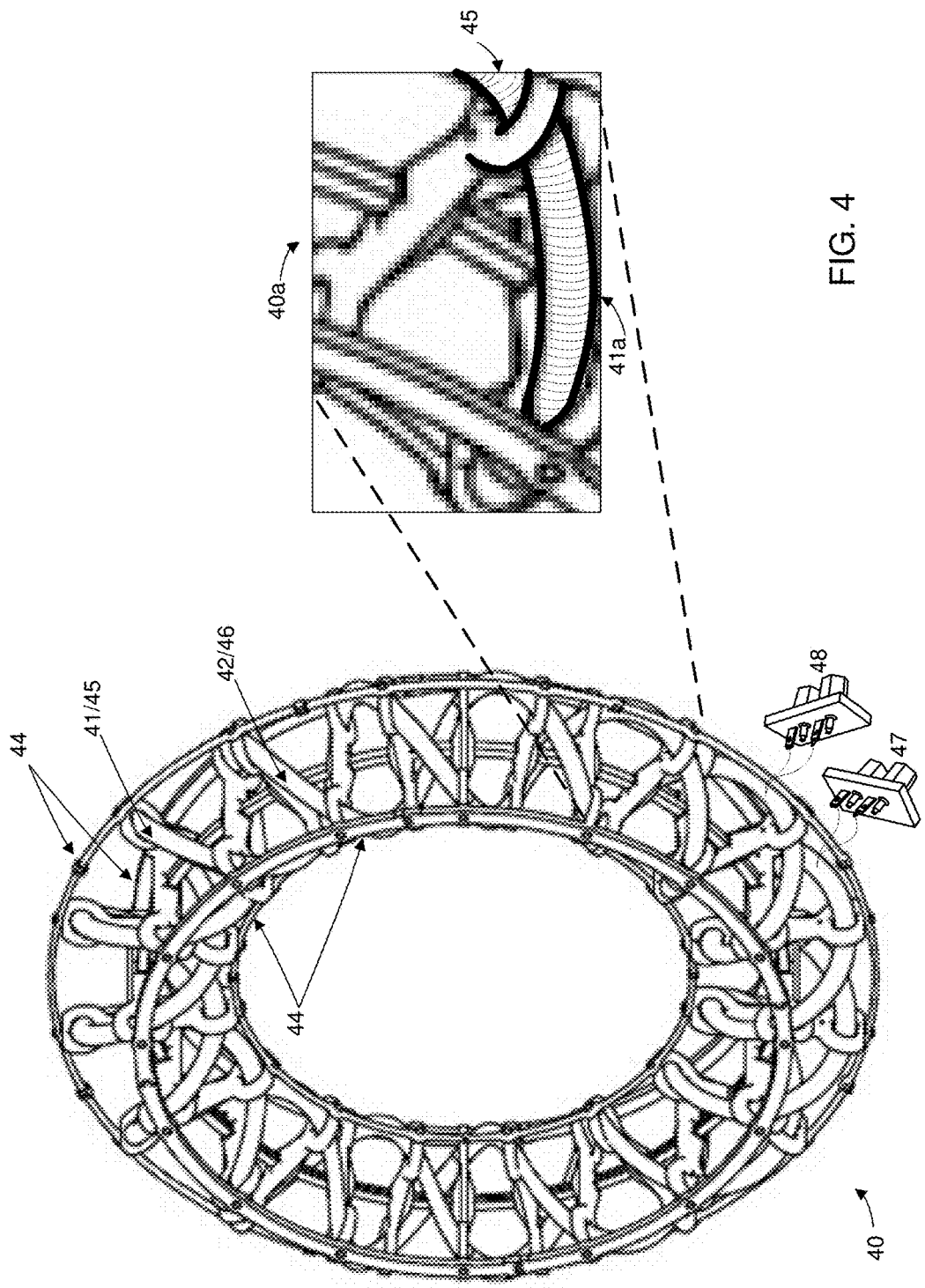
FIG. 4 illustrates an exemplary body including two intertwined helically wound runners, the body arranged to form a toroidal shape.

FIG. 4 illustrates an exemplary body 40 including two intertwined helically wound runners, a first runner 41 and a second runner 42, in the shape or form of a double helix, the body 40 being arranged to form a toroidal shape which may be similar to toroidal shape 10 as shown in FIG. 1. Body 40 may be arranged such that the axis of the double helix is not straight but curved, e.g. in a circle or oval. The runners of body 40 may be supported by support structures 44. As shown in a view 40a that illustrates a magnified section of body 40, which includes a section 41a of runner 41, a wire 45 may be wound around runner 41. In some embodiments, wire 45 may be wound clockwise. In some embodiments, wire 45 may be wound counter-clockwise. Wire 45 may be conductive. Wire 45 may be too fine to be visible in a figure without magnification. A wire such as wire 45 may be insulated, uninsulated, or partially insulated and partially uninsulated, as may any wire listed in any figure included in this description. As used herein, a "wire" may include a set of twisted wires (which may interchangeably be referred to as a "twisted wire"), including but not limited to a set of two twisted wires. A wire 46 may be wound around runner 42 in a manner similar to wire 45 and runner 41. A connector 47 may be electrically coupled to twisted wire 45. For example, as shown in FIG. 4, both ends of twisted wire 45 may be electrically coupled to connector 47. A connector 48 may be electrically coupled to twisted wire 46. For example, as shown in FIG. 4, both ends of twisted wire 46 may be electrically coupled to connector 48. One or more power sources and/or current sources (not shown in FIG. 4) may be electrically coupled to connector 47 and/or connector 48 to supply current to twisted wire 45 and/or twisted wire 46, respectively, such that an electromagnetic effect (e.g. an electromagnetic field) is created around and/or near body 40. In one or more embodiment of the invention, wherein the first runner has a first surface, wherein the second runner has a second surface, wherein the first conductive wire is arranged at a fixed distance from the first surface of the first runner, and wherein the second conductive wire is arranged at a second fixed distance from the second surface of the second runner.

In some implementations, a system may include one or more bodies that are similar to body 40. Such a system may be configured to generate and/or create an electromagnetic effect around and/or near the one or more bodies. By virtue of this electromagnetic effect, such a system may be used for agricultural applications, e.g. to promote growth of organisms, and/or be used for other applications. In some implementations, such a system may be used to improve and/or promote the health of organisms. As shown in FIG. 4, by way of non-limiting example, body 40 may be arranged such that body 40 is substantially vertical. For example, the plane that bisects the toroidal shape of body 40 into two similar, congruent, circular, and/or isometric halves (e.g. as described in relation to FIG. 1) may be arranged such that the plane is substantially vertical. In some embodiments, the plane that bisects the toroidal shape of body 40 into two similar, congruent, circular, and/or isometric halves (e.g. as described in relation to FIG. 1) may be arranged such that the plane is substantially horizontal.

In some implementations, body 40 may be constructed such that its diameter is about 4 inches, about 6 inches, about 8 inches, about 10 inches, about 1 foot, about 18 inches, about 2 feet, about 30 inches, about 3 feet, about 4 feet, about 5 feet, about 6 feet, about 7 feet, about 8 feet, about 9 feet, about 10 feet, and/or other sizes. In some implementations, body 40 may have a diameter of about 20 inches. In some implementations, body 40 may have a diameter of about 50 or 60 inches.

Figure 5:
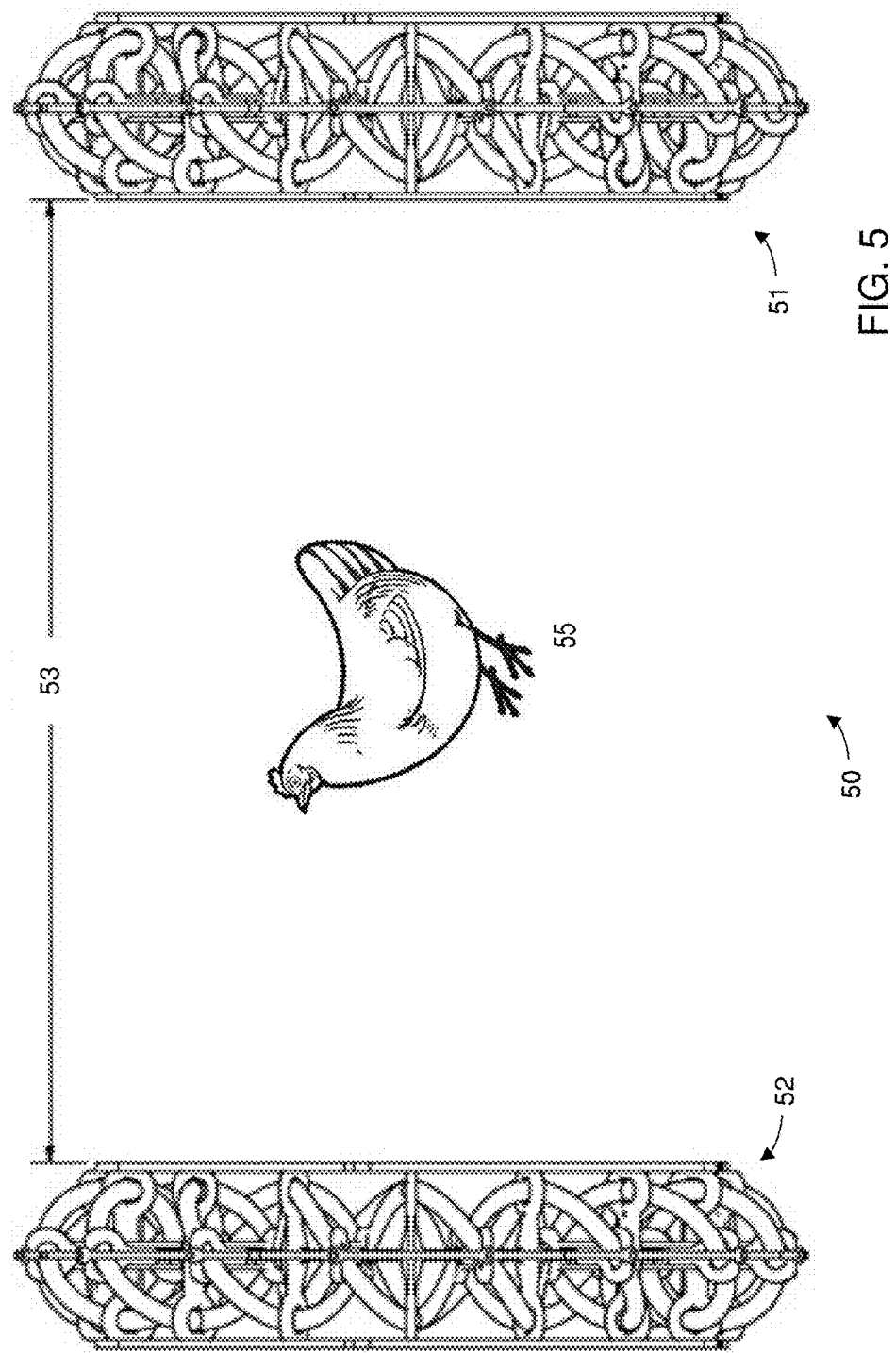
FIG. 5 illustrates an arrangement of two exemplary bodies that each include two intertwined helically wound runners.

FIG. 5 illustrates an exemplary system 50 that includes an arrangement of two exemplary bodies 51 and 52 near an organism 55. The depiction of organism 55 as a single element, in this case a chicken, is not meant to be limiting in any way. Bodies 51 and 52 may be arranged such that multiple organisms are positioned between the bodies. The depiction of a chicken is not intended to be limiting in any way. For example, any cultivated lifeform(s)—not just animals—known to agriculture may be used as organism 55, including but not limited to chicken, cow, pig, lamb, goat, bird, fish, crustacean, mollusk, reptile, and/or other animals.

Each of body 51 and body 52 may include two intertwined helically wound runners. In some implementations, body 51 may be similar to body 40 shown in FIG. 4. By way of non-limiting example, components shown in FIG. 4 may be included in system 50 (as well as system 60 in FIG. 6, system 70 in FIG. 7, and system 80 in FIG. 8, and vice versa), such as a first runner, a second runner, one or more support structures, a first twisted conductive wire wound around the first runner, a second twisted conductive wire wound around the second runner, a first connector, a second connector, one or more power sources and/or current sources, and/or other components. By way of non-limiting example, the vertical arrangement of bodies 51 and 52 may be similar to body 40 shown in FIG. 4. By way of non-limiting example, this disclosure envisions combining elements shown in different figures.

Referring to FIG. 5, in some implementations, body 52 may be similar to body 40 shown in FIG. 4. Referring to FIG. 5, body 51 and body 52 may be arranged such that the first plane that bisects the toroidal shape of body 51 (into similar circular halves) and the second plane that bisects the toroidal shape of body 52 (into similar circular halves) are parallel to each other. In some implementations, body 51 and body 52 may be arranged such that the axis through the hole (not shown in FIG. 5 due to viewpoint) of the toroidal shape of body 51 (as described in relation to FIG. 1) is aligned with the axis through the hole (not shown due to viewpoint) of the toroidal shape of body 52.

In some implementations, body 51 and body 52 may be arranged a distance 53 apart. In some implementations, distance 53 may be about 4 inches, about 6 inches, about 1 foot, about 18 inches, about 2 feet, about 30 inches, about 3 feet, about 4 feet, about 5 feet, about 6 feet, about 7 feet, about 8 feet, about 9 feet, about 10 feet, and/or other distances. In some implementations, distance 53 may be about 10 feet, about 20 feet, about 50 feet, about 100 feet, about 200 feet, about 500 feet, about 1000 feet, about 2000 feet, about 5000 feet, about 10000 feet, and/or other distances. For example, body 51 and body 52 may be placed at opposite ends of a chicken house, such that the generated electromagnetic effect may promote growth across the entire length of the chicken house.

In some implementations, twisted conductive wires wound individual runners may operate as antennae and effectively broadcast frequencies below 10 MHz. In some implementations, the broadcast frequency may depend on the wire length. In systems having multiple bodies, the electromagnetic field between the bodies may be reduced and/or partially cancelled, while maintaining promotion of growth as explained elsewhere in this disclosure.

In some implementations, the double helix of body 51 may have the opposite handedness as the double helix of body 52. In some implementations, the double helix of body 51 may have the same handedness as the double helix of body 52. In some embodiments, the one or more conductive wires wound around the one or more runners of body 51 may be wound clockwise. In some embodiments, the one or more conductive wires wound around the one or more runners of body 51 may be wound counter-clockwise. In some embodiments, the one or more conductive wires wound around the one or more runners of body 52 may be wound in the same direction as those of body 51. In some embodiments, the one or more conductive wires wound around the one or more runners of body 52 may be wound in the opposite direction as those of body 51. For example, in a system having opposite wiring of the conductive wires in different bodies, the electromagnetic field between the bodies may be reduced and/or partially cancelled, while maintaining promotion of growth as explained elsewhere in this disclosure.

Figure 10:
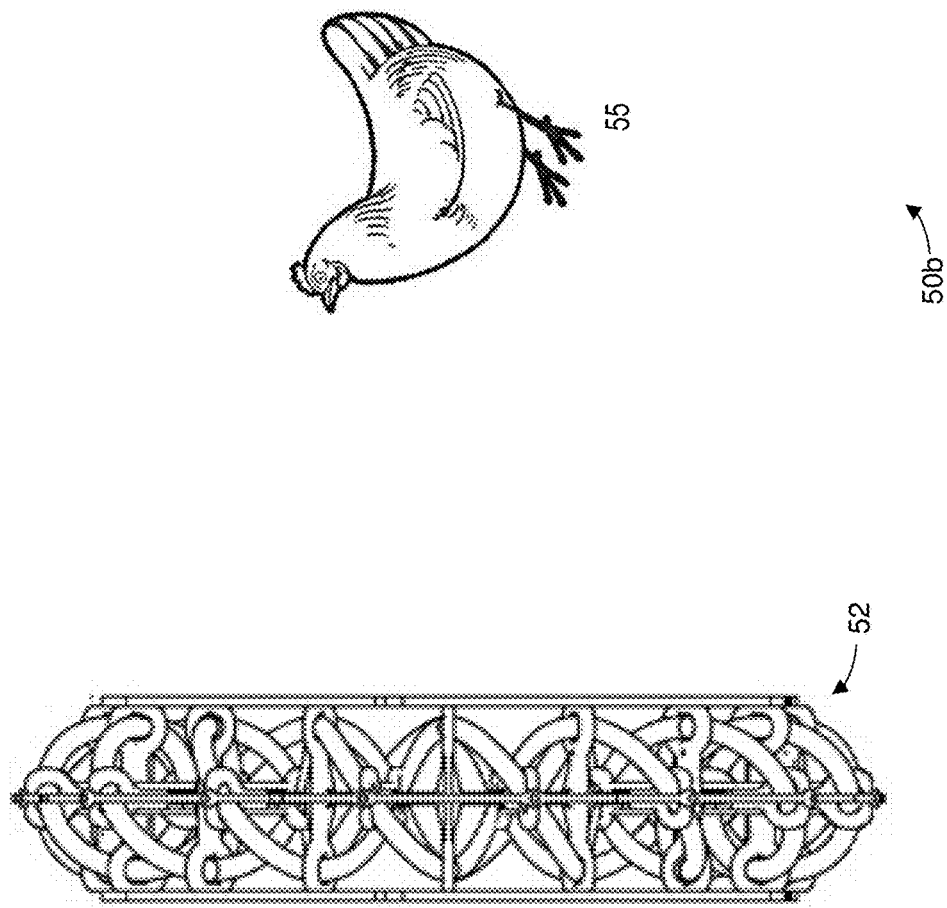
FIGS. 10 and 11 illustrate arrangements of one exemplary body that includes two intertwined helically wound runners.

FIG. 10 illustrates an exemplary system 50*b* similar to system 50 of FIG. 5, but with only one exemplary body 52 near an organism 55.

Figure 6:
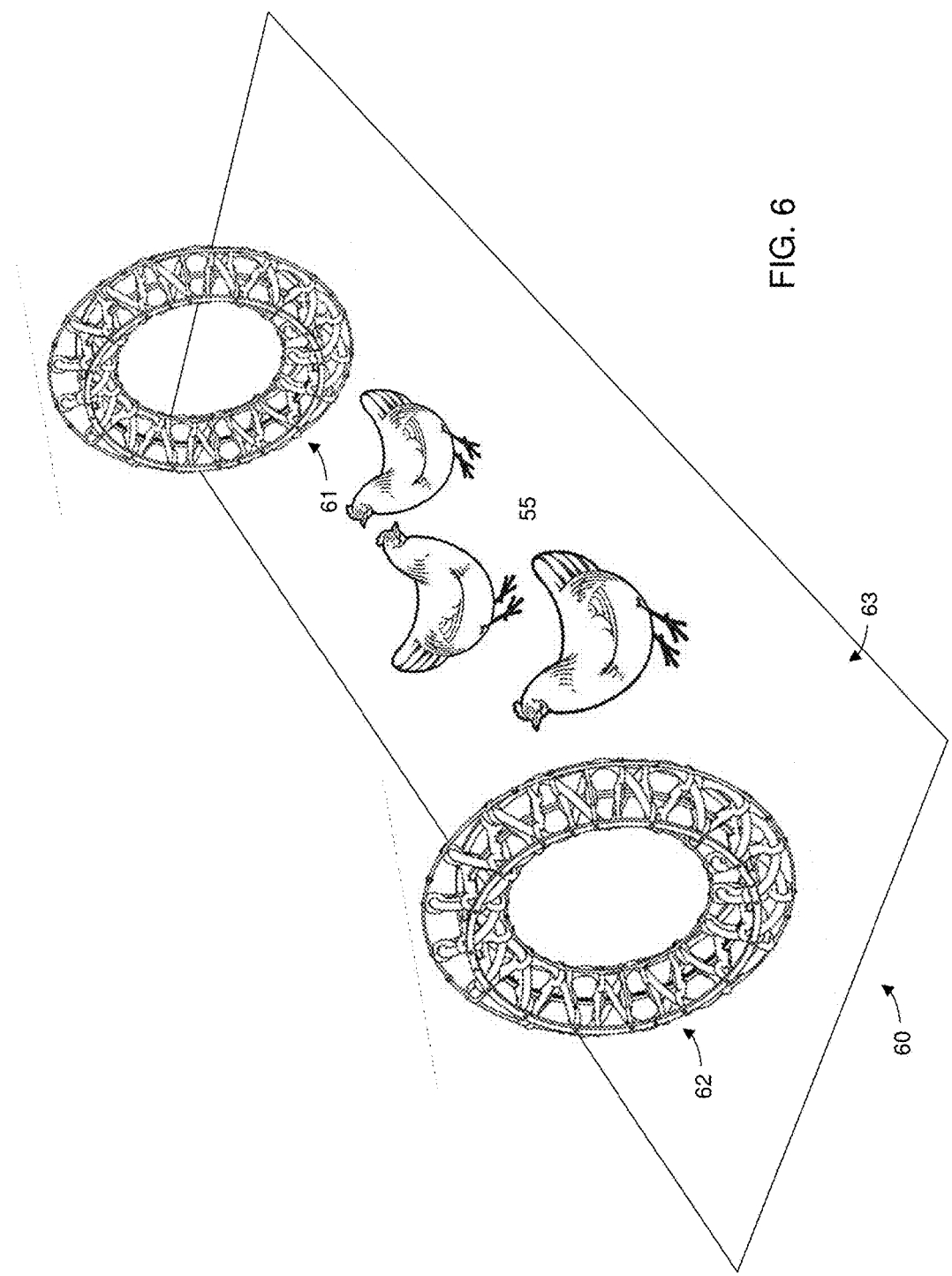
FIG. 6 illustrates an arrangement of two exemplary bodies that each include two intertwined helically wound runners.

FIG. 6 illustrates an exemplary system 60 that includes an arrangement of two exemplary bodies 61 and 62 near an organism 55. The depiction of organism 55 as three chickens is not meant to be limiting in any way. Bodies 61 and 62 may be arranged such that multiple organisms are positioned between the bodies. Each of bodies 61 and 62 may include two intertwined helically wound runners. Note that some components such as connectors and current sources (described elsewhere in this disclosure) are not depicted in FIG. 6, but may be included in system 60. In some implementations, body 61 may be similar to body 51 shown in FIG. 5 and/or body 40 shown in FIG. 4. In some implementations, body 62 may be similar to body 52 shown in FIG. 5 and/or body 40 shown in FIG. 4. Referring to FIG. 6, body 61 and body 62 may be arranged on a surface or structure 63, e.g. a tabletop or a floor. By way of non-limiting example, the vertical arrangement of bodies 61 and 62 may be similar to body 40 shown in FIG. 4. In some implementations, system 60 may be configured to support organisms 55 that may benefit from being subjected to an electromagnetic effect generated by system 60. The depiction and number of organisms in FIG. 6 is not intended to be limiting in any way.

In some implementations, body 61 and body 62 may be arranged such that the first plane that bisects the toroidal shape of body 61 and the second plane that bisects the toroidal shape of body 62 are parallel to each other. In some implementations, body 61 and body 62 may be arranged such that the axis through the hole of the toroidal shape of body 61 is aligned with (e.g. in the same three-dimensional position as) the axis through the hole of the toroidal shape of body 62, and/or perpendicular to the bisecting planes.

Figure 11:
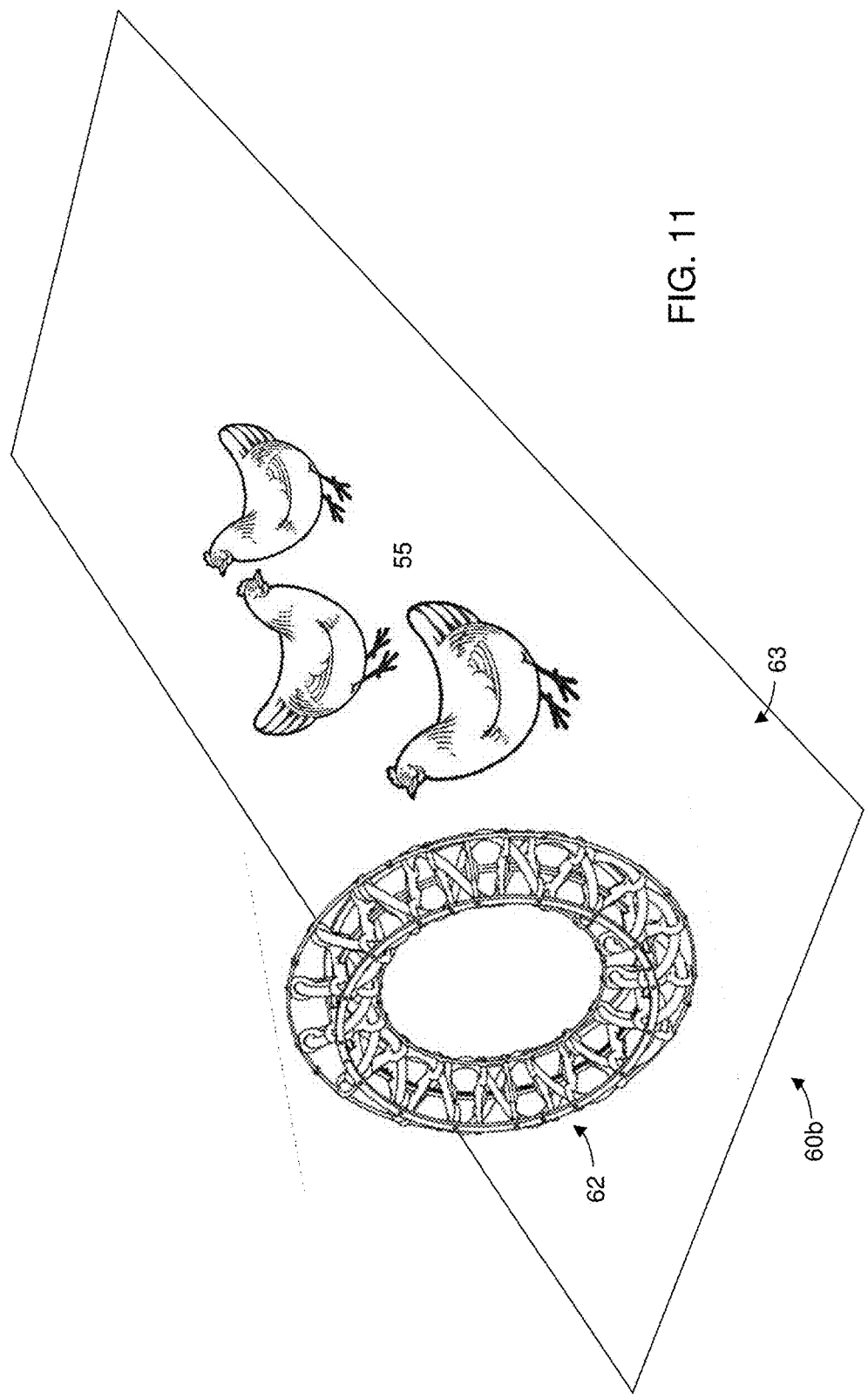

FIG. 11 illustrates an exemplary system 60*b* similar to system 60 of FIG. 6, but with only one exemplary body 62 near one or more organisms 55.

Figure 7:
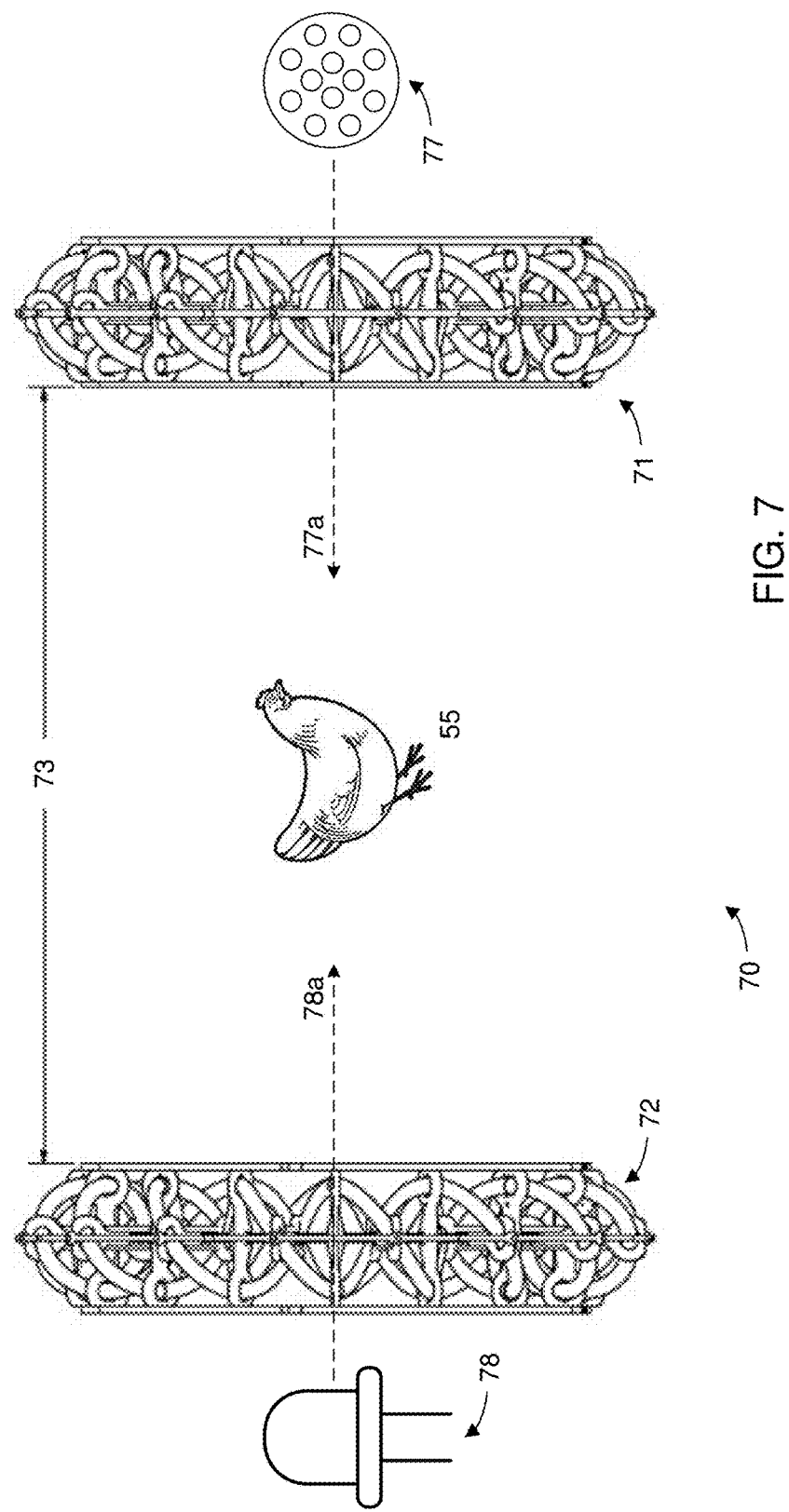
FIG. 7 illustrates an arrangement of multiple light sources and two exemplary bodies that each include two intertwined helically wound runners.

FIG. 7 illustrates an exemplary system 70 that includes an arrangement of multiple light sources 77 and 78 and two exemplary bodies 71 and 72 near an organism 55. The depiction of organism 55 as a single element, in this case a chicken, is not meant to be limiting in any way. Bodies 71 and 72 may be arranged such that multiple organisms are positioned between the bodies. Each of body 71 and body 72 may include two intertwined helically wound runners. In some implementations, body 71 may be similar to body 61 shown in FIG. 6, body 51 shown in FIG. 5, and/or body 40 shown in FIG. 4. In some implementations, body 72 may be similar to body 62 shown in FIG. 6, body 52 shown in FIG. 5, and/or body 40 shown in FIG. 4. By way of non-limiting example, the vertical arrangement of bodies 71 and 72 may be similar to body 40 shown in FIG. 4. Referring to FIG. 7, body 71 and body 72 may be arranged such that the first plane that bisects the toroidal shape of body 71 and the second plane that bisects the toroidal shape of body 72 are parallel to each other. In some implementations, body 71 and body 72 may be arranged such that the axis through the hole (not shown due to viewpoint) of the toroidal shape of body 71 (as described in relation to FIG. 1) is aligned with the axis through the hole (not shown due to viewpoint) of the toroidal shape of body 72.

In some implementations, body 71 and body 72 may be arranged a distance 73 apart. In some implementations, distance 73 may be about 4 inches, about 6 inches, about 1 foot, about 18 inches, about 2 feet, about 30 inches, about 3 feet, about 4 feet, about 5 feet, about 6 feet, about 7 feet, about 8 feet, about 9 feet, about 10 feet, and/or other distances. In some implementations, distance 73 may be about 10 feet, about 20 feet, about 50 feet, about 100 feet, about 200 feet, about 500 feet, about 1000 feet, about 2000 feet, about 5000 feet, about 10000 feet, and/or other distances. For example, body 71 and body 72 may be placed at opposite ends of a chicken house, such that the generated electromagnetic effect may promote growth across the entire length of the chicken house.

In some implementations, system 70 may include light source 77, light source 78, and/or other sources of electromagnetic radiation. In some implementations, light source 77 may be arranged and/or disposed in proximity of body 71. In some implementations, light source 78 may be arranged and/or disposed in proximity of body 72. In some implementations, light source 78 may emit a narrow spectrum of electromagnetic radiation. For example, light source 78 may include a laser and/or another light source that emits a narrow spectrum of electromagnetic radiation. In some implementations, light source 78 may be configured to be pulsed at a particular frequency, e.g., synchronized with one or more frequencies used to supply alternating current to the twisted wires wound around the runners of a body. In some implementations, light source 78 may be configured to be pulsed at a particular frequency, e.g., the beat frequency that is created as described in this disclosure. In some implementations, light source 78 may be configured to be pulsed using a sine wave, a square wave, and/or another type of control. In some implementations, light source 78 may be configured to be pulsed using different duty cycles, e.g., 50/50, 40/60, 30/70, 20/80, 10/90, and/or another duty cycle. In some implementations, the addition of one or more light sources reduced the regeneration period of certain organic matter or organisms (e.g. planarians) by 25% (e.g. from 24 hours to 18 hours).

In some implementations, a filter (not shown) having a narrow bandwidth may be placed between light source 78 and body 72 such that electromagnetic radiation emitted by light source 78 (at least along direction 78*a* as shown in FIG. 7, and/or in other directions) passes through the filter prior to traversing through body 72 and/or impinging on any matter and/or object, such as organism 55, that is disposed between body 72 and body 71. In some implementations, light source 77 may emit a narrow spectrum of electromagnetic radiation. For example, light source 77 may include one or more light emitting diodes (LEDs) and/or another light source that emits a narrow spectrum. In some implementations, a filter (not shown) having a narrow bandwidth may be placed between light source 77 and body 71 such that electromagnetic radiation emitted by light source 77 (at least along direction 77*a* as shown in FIG. 7, and/or in other directions) passes through the filter prior to traversing through body 71 and/or impinging on any matter and/or object, such as organism 55, that is disposed between body 72 and body 71. In some implementations, one or more filters may be disposed in proximity of organism 55 such that electromagnetic radiation emitted by one or more light sources passes through one or more filters prior to impinging on organism 55.

In some implementations, system 70 may include multiple similar light sources. For example, system 70 may include two light sources that are similar to light source 77, or two light sources that are similar to light source 78, and/or two light sources that are similar to each other. Referring to FIG. 7, the illustration of light source 78 and light source 78 in FIG. 7 is merely schematic, and not intended to be limiting with regard to the functionality of the light sources.

Figure 8:
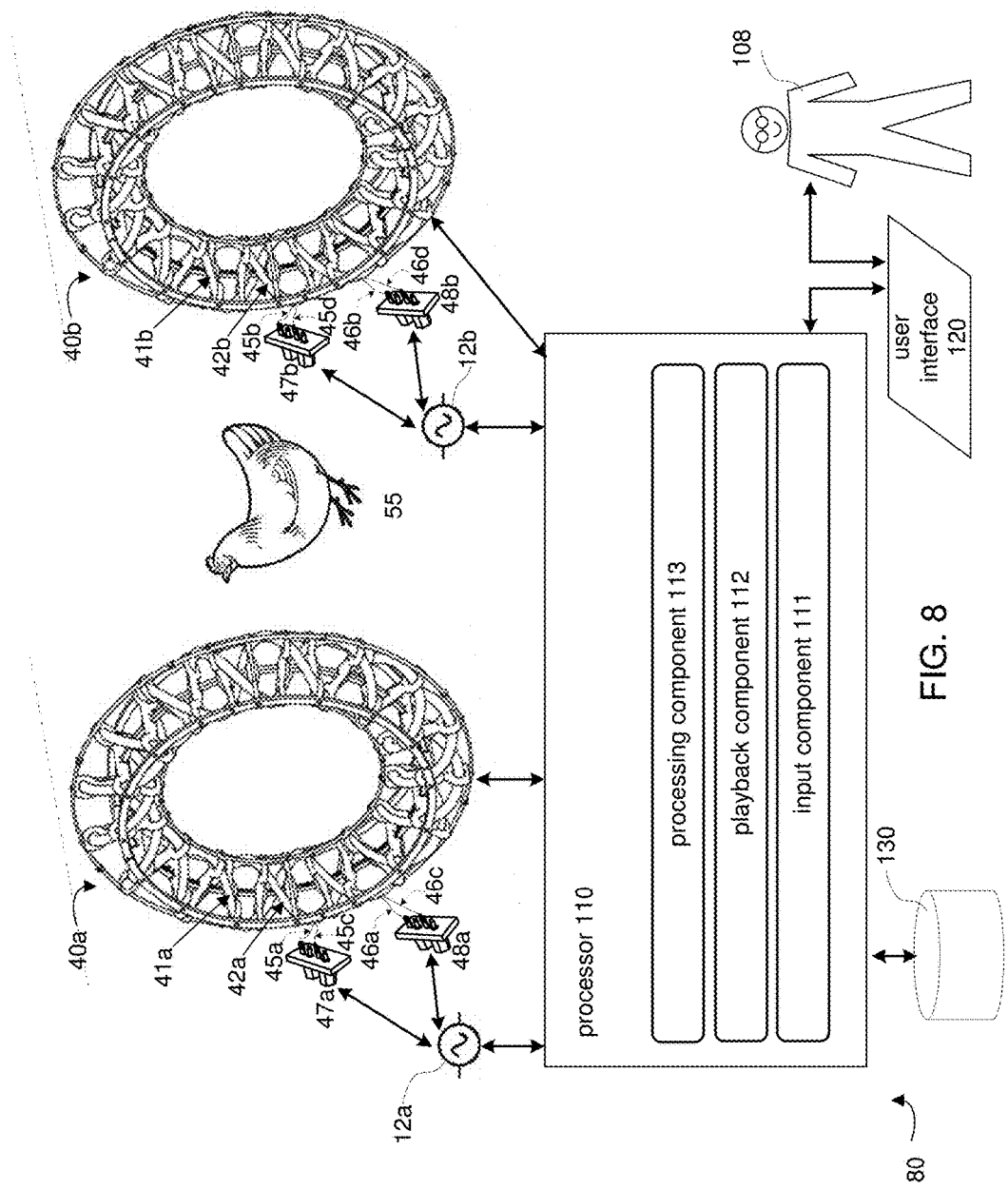
FIG. 8 illustrates a system that includes two exemplary bodies that each include two intertwined helically wound runners.

FIG. 8 illustrates an exemplary system 80 that includes one or more of a processor 110, a user interface 120, electronic storage, connectors 47*a*, 47*b*, 48*a*, and 48*b*, power sources 12*a* and 12*b*, bodies 40*a* and 40*b* that each including two intertwined helically wound runners sharing the same circular axis, both runners having conductive wires spirally wound therearound. System 80 may include body 40*a*. In some implementations, body 40*a* may be similar to body 40 shown in FIG. 4. By way of non-limiting example, the vertical arrangement of bodies 40*a* and 40*b* may be similar to body 40 shown in FIG. 4. In some embodiments, the arrangement of bodies 40*a* and 40*b* may be substantially horizontal.

Body 40*a* may include a first runner 41*a* and a second runner 42*a*. A first conductive twisted wire may be wound around first runner 41*a* and electrically coupled to connector 47*a* via twisted wire ends 45*a* and 45*c*. A second conductive twisted wire may be wound around second runner 42*a* and electrically coupled to connector 48*a* via twisted wire ends 46*a* and 46*c*. Connectors 47*a* and 48*a* may be electrically coupled to power source 12*a* such that one or more electric currents are supplied to the twisted wires wound around first runner 41*a* and second runner 42*a*, such that an electromagnetic effect (e.g. an electromagnetic field) is created around and/or near body 40*a*. Body 40*a* may be arranged near organism 55. System 80 may include body 40*b*. In some implementations, body 40*b* may be similar to body 40 shown in FIG. 4. Body 40*b* may include a first runner 41*b* and a second runner 42*b*. A first conductive twisted wire may be wound around first runner 41*b* and electrically coupled to connector 47*b* via twisted wire ends 45*b* and 45*d*. A second conductive twisted wire may be wound around second runner 42*b* and electrically coupled to connector 48*b* via twisted wire ends 46*b* and 46*d*. Connectors 47*b* and 48*b* may be electrically coupled to power source 12*b* such that one or more electric currents are supplied to the twisted wires wound around first runner 41*b* and second runner 42*b*, such that an electromagnetic effect (e.g. an electromagnetic field) is created around and/or near body 40*b*. In some implementations, power may be supplied to connectors 47*a*, 47*b*, 48*a*, and 48*b* via a single power source. Body 40*b* may be arranged near organism 55. In some implementations, bodies 40*a* and 40*b* may be arranged such that organism 55 is positioned between the bodies. The depiction of organism 55 as a single element, in this case a chicken, is not meant to be limiting in any way. The depiction of a chicken is not intended to be limiting in any way.

Regarding systems 40, 50, 60, 70, and 80, any two intertwined helically wound runners may share the same axis, be congruent, and/or differ by a translation along the axis, e.g. measuring half the pitch.

By way of non-limiting example, additional structures and/or features of any bodies in systems 40, 50, 60, 70, and 80 may be described in U.S. Pat. No. 8,653,925, entitled "Double Helix Conductor," which issued Feb. 18, 2014, which is hereby incorporated into this disclosure by reference in its entirety. This patent may also be referred to as "the '925 patent" herein.

The runners in systems 40, 50, 60, 70, and 80 may be manufactured from one or more of plastic, plastic plated with metals including copper, nickel, iron, soft iron, nickel alloys, fiberoptic materials, and/or other materials (or combinations thereof). In some implementations, one or more runners may be are manufactured from non-conductive material.

The number of turns of a set of twisted wires per inch and/or per helical revolution of a runner may be characteristic measurements/features of an implementation of any of the systems described herein. In some implementations, the number of twists per inch of a twisted wire may be about 2, about 5, about 10, about 20, about 50, about 100, about 150, about 200, about 250, and/or another suitable number of twists. In some implementations, the frequency characteristics of an alternating current and/or the corresponding generated electromagnetic effect or field may be based on, proportional to, and/or otherwise related to the number of twists of a twisted wire. For example, a higher number of twists per inch may correspond to a higher operating frequency for the alternating current and/or the corresponding generated electromagnetic effect and/or field. In some implementations, multiple twisted wires (e.g. a first twisted wire wound around a first runner and a second twisted wire wound around a second runner) may have the same direction of twisting, and/or a different direction of twisting. In some implementations, multiple wires (e.g. twisted wires) may be wound around the same runner. In some implementations, a wire may be wound around some or all of one or more struts.

The electric currents supplied to the conductive wires wound around the first and second runner of any of the bodies in systems 40, 50, 60, 70, and 80 may flow in the same direction or the opposite direction. For alternating currents, operating frequencies ranging from more than 0 Hz to about 40 GHz are contemplated. The operating frequencies for the conductive wires wound around the first and second runner of any of the bodies in systems 40, 50, 60, 70, and 80 may be the same or different. Other electrical operating characteristics of the supplied currents, such as phase, amplitude, power-level, and/or other operating characteristics, may be the same or different. Systems 40, 50, 60, 70, and 80 may be used to exploit the electromagnetic field that is created when electrical power is supplied to one or more wires of one or more bodies.

Referring to FIG. 7, the electromagnetic radiation emitted by one or both of light sources 77 and 78 may include specific wavelengths. By virtue of using specific wavelengths, emitted electromagnetic radiation may produce specific biological effects. This biophysical principle may be referred to as photo-bio-modulation.

In some implementations, the conductive wires wound around the first and second runner of body 40*a* are supplied with a first alternating current, e.g. of 216 Hz, and the conductive wires wound around the first and second runner of body 40*b* are supplied with a second alternating current, e.g., of 864 Hz. In some implementations, the currents supplied to body 40*a* and body 40*b* may be 180 degrees out of phase. Supply of the first and second current may create a beat frequency of 432 Hz (corresponds to an "A" note). In some implementations, using a similar approach, beat frequencies of 486 Hz, 512 Hz, 576 Hz, 648 Hz, 729 Hz, 768 Hz, and/or other frequencies may be used, which correspond to "B," "C," "D," "E," "F," and "G" notes, respectively. In some implementations, the double helix of body 40*a* may have the opposite handedness as the double helix of body 40*b*. In some implementations, the double helix of body 40*a* may have the same handedness as the double helix of body 40*b*.

In some implementations, by combining elements of FIG. 7 and FIG. 8, the one or more light sources may be configured to emit electromagnetic radiation that predominantly includes visible wavelengths. Particular wavelengths may be selected to correspond (and be supplied contemporaneously) with particular beat frequencies. For example, the combination of using a beat frequency of 432 Hz and one or more light sources emitting electromagnetic radiation having a predominant wavelength of 631 nm has been found useful in various applications. Other useful combinations include 486 Hz and 561 nm, 512 Hz and 533 nm, 576 Hz and 473 nm, 648 Hz and 421 nm, 729 Hz and 748 nm, and 768 Hz and 710 nm. These examples are not intended to be limiting.

Any combination of one or more generated electromagnetic effects (e.g. an electromagnetic effect and/or field generated as described in this disclosure), emitted electromagnetic radiation, and/or biological effects produced by virtue of proximity (as described in this disclosure) may be used in applications.

Applications for any of the systems described herein may include affecting growth and/or growth rate of plants, livestock, samples, tissue, stem cells, living cells, and/or other (organic) matter, medical applications, therapeutic applications, energy production, energy conversion, energy transformation, adenosine triphosphate (ATP) production, ATP transfer, ATP processing, and/or other applications.

Promotion of growth may include one or more of an increased growth rate, an increased maximum growth level, an increased maximum yield, a shorter duration to reach maturity, and an increased feed conversion rate. Using any of the electrical systems described herein, the growth rate, or range of typical growth rates, of the particular type of plant may be increased to a higher growth rate, or higher range of growth rates, for the particular plant. A unit of growth rate may be inch/day, or another unit expressing some length, area, volume, or size per unit of time, and/or another appropriate unit. For some embodiments, such as e.g. an embodiment using algae or suitable similar plants, growth rate may be expressed though lipid production rate, starch content production rate, biomass content production rate.

For example, a specific type of organism may have a typical maximum growth level, under growing conditions that lack a significant electromagnetic field. Using any of the electrical systems described herein, the maximum growth level, or range of typical maximum growth levels, of the specific type of organism may be increased to a higher maximum growth level, or higher range of maximum growth levels, for the specific organism. Maximum growth level may be expressed in inches, square inches, liters, kilograms, lipid content, and/or another unit expressing some length, area, volume, weight, or size, and/or another appropriate unit.

For example, a particular type of organism may have a typical maximum yield, under growing conditions that lack a significant electromagnetic field. Using any of the electrical systems described herein, the maximum yield, or range of typical maximum yields, of the particular type of organism may be increased to a higher maximum yield, or higher range of maximum yields, for the particular organism. Maximum yield may be expressed in volume or weight per area and/or period, such as kilogram/square feet, or pounds per acre per week, and/or other units as appropriate.

For example, a particular type of organism may have a typical feed conversion (e.g., a rate or ratio), under farming conditions that lack a significant electromagnetic field. Using any of the electrical systems described herein, the maximum feed conversion, or range of typical maximum feed conversions, of the particular type of organism may be increased to a higher maximum feed conversion, or higher range of maximum feed conversions, for the particular organism. In some implementations, feed conversion may be expressed as a percentage of feed that is converted to mass or weight of the organisms, and/or other units as appropriate.

In some implementations, a system including any of the components shown in FIGS. 4-8 (and/or multiple instances thereof) may be used as a component in an electrical circuit, performing one or more functions and/or applications including a (broadcast) antenna, a (tunable) inductor, a (Tesla) coil, a transformer, a transducer, a transistor, a resistor, a solenoid, a stator for an electrical motor, an electromagnet, an electromagnetic pulse generator, an electromagnetic actuator, an energy conversion device, a position servomechanism, a generator, a stepping motor, a DC motor, a (contact-free) linear drive, an axial flux device, a measurement device for magnetic permeability, a dipole magnet, a device to alter electron and/or particle trajectory, and/or any combination thereof.

Referring to FIG. 8, system 80 may include one or more of user interface 120, one or more physical processors 110, electronic storage 130, one or more power sources and/or current sources (e.g. power source 12*a* and power source 12*b*), an input component 111, a playback component 112, a processing component 113, and/or other components.

In some implementations, a system similar to system 80 may include one or more sensors (not shown in FIG. 8). The one or more sensor may be configured to generate output signals conveying information. The information may include electrophysiological information and/or other information. In some implementations, the one or more sensors may include one or more of an audio sensor, a microphone, a stethoscope, a pressure sensor, a motion sensor, a proximity sensor, an electromagnetic sensor, an electrode, a temperature sensor, a current sensor, an optical sensor, an electro-optical sensor, and/or other sensors or combinations thereof. In some implementations, the one or more processors 110 may be configured to provide information-processing capabilities and/or execute computer program components, including but not limited to input component 111, playback component 112, processing component 113, and/or other components. By way of non-limiting example, additional structures and/or features of the one or more sensors, processor 110, user interface 120, electronic storage 130, input component 111, playback component 112, and/or processing component 113, may be described in U.S. patent application Ser. No. 14/194,412, entitled "Health Applications for Using Bio-Feedback to Control an Electromagnetic Field," which was filed Feb. 28, 2014, which is hereby incorporated into this disclosure by reference in its entirety. This application may also be referred to as "the '412 application" herein.

In some implementations, one or more currents supplied to connectors 47*a*, 47*b*, 48*a*, and 48*b* may correspond to one or more sensor-generated output signals. In some implementations, the one or more currents may correspond to one or more signals generated by a transducer and/or one or more other components of system 80. In some implementations, an alternating current supplied to body 40*a* and/or 40*b* may include a carrier signal and a modulating signal. In some implementations, carrier signals used for the alternating current may be radio-frequency signals. As used herein, radio frequency may refer to frequencies between about 30 kHz and about 30 GHz. In some implementations, the modulating signals may have a lower frequency than the carrier signal. For example, the modulating signal may be in the 10-100 MHz range, the 1-10 MHz range, the 100 kHZ-1 MHz range, the 10-100 KHz range, the acoustic range, the telephone range, and/or another suitable range. In some implementations, the modulating signal for the alternating current may be modulated through one or more of amplitude modulation, frequency modulation, phase modulation, digital modulation, and/or other types of modulation. As used herein, the term "acoustic range" may refer to frequencies between about 20 Hz and about 20 kHz. As used herein, the term "telephone range" may refer to frequencies between about 300 Hz and about 3300 Hz.

In some embodiments, the one or more currents supplied to connectors 47*a* and 48*a* may run in the same direction as the one or more currents supplied to connectors 47*b* and 48*b*. In some embodiments, the one or more currents supplied to connectors 47*a* and 48*a* may run in the opposite direction as the one or more currents supplied to connectors 47*b* and 48*b*. For example, in a system having opposite currents running through the conductive wires in different bodies, the electromagnetic field between the bodies may be reduced and/or partially cancelled, while maintaining promotion of growth as explained elsewhere in this disclosure.

In some implementations, the one or more frequencies included in an alternating current supplied to body 40*a* and/or 40*b* may be based on audio recordings of a note, tone, or chord, generated by a frequency generator and/or a (musical) instrument. For example, a first frequency may be based on the sound of a piano playing an A above middle C (also referred to as A4, which may include sound having a frequency of about 432 Hz, depending on the tuning system used). For example, a second frequency may be based on the sound of some instrument (e.g. a piano) playing a note forming a harmonious interval with A4, which may include sound having a frequency of about 648 Hz. This tuning may be referred to as Pythagorean tuning. Mathematically perfect tuning may combine notes having a 3:2 ratio. Different types of tuning (or tuning systems), including but not limited to equal tempered tuning, may be used and considered within the scope of this disclosure.

Processor 110 may include one or more of a digital processor, an analog processor, a digital circuit designed to process information, a central processing unit, a graphics processing unit, an analog circuit designed to process information, and/or other mechanisms for electronically processing information. Although processor 110 is shown in FIG. 8 as a single entity, this is for illustrative purposes only. In some implementations, processor 110 may include a plurality of processing units.

It should be appreciated that although components 111-113 are illustrated in FIG. 8 as being co-located within a single processing unit, in implementations in which processor 110 includes multiple processing units, one or more of components 111-113 may be located remotely from the other components. The description of the functionality provided by the different components 111-113 described herein is for illustrative purposes, and is not intended to be limiting, as any of components 111-113 may provide more or less functionality than is described. For example, one or more of components 111-113 may be eliminated, and some or all of its functionality may be incorporated, shared, integrated into, and/or otherwise provided by other ones of components 111-113. Note that processor 110 may be configured to execute one or more additional components that may perform some or all of the functionality attributed below to one of components 111-113.

Input component 111 may be configured to obtain information, e.g. from one or more digital audio files, or, alternatively and/or simultaneously, based on sensor-generate output signals. In some implementations, the information may be obtained from storage, e.g. from electronic storage. Information obtained from storage may include electronic audio files in any format, including but not limited to MP3, WMA, WAV, AIFF, and/or other audio formats. In some implementations, information may be obtained from sound sources including frequency generators, phonographs, CD-players, DVD players, AM radio, FM radio, and/or other sound sources.

Processing component 113 may be configured to process the obtained information from input component 111. In some implementations, processing component 113 may be configured to generate a processed signal based on the obtained information from input component 111. For example, processing component 113 may convert, filter, modify, and/or otherwise transform information or signals from input component 111 to generate the processed signal.

Playback component 112 may be configured to produce sound signals based on one or more of the obtained information from input component 111 and/or the processed signal from processing component 113. The sound signals produced by playback component 112 may be coupled electrically to the leads/ends of one or more conductive wires wound around one or more runners of body 40*a* and/or 40*b* such that the induced current corresponds to and/or is based on the sound signals. Alternatively, and/or simultaneously, the induced current may be controlled by and/or based on the sound signals produced by playback component 112. In some implementations, the sound signals produced by playback component 112 may be amplified by an amplifier before being electrically coupled to the leads/end of one or more conductive wires. In some preferred implementations, the amplifier may be an audio amplifier ranging between 100 W and 400 W. Other types of amplifiers and/or amplifiers having a different power range are also contemplated.

Electronic storage 130 in FIG. 8 comprises electronic storage media that electronically stores information. The electronic storage media of electronic storage 130 may include one or both of system storage that is provided integrally (i.e., substantially non-removable) with system 80 and/or removable storage that is connectable to system 80 via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 80 to function properly. For example, electronic storage 130 may store sound information and/or electronic audio files (as discussed elsewhere herein), and/or other information. Electronic storage 130 may be a separate component within system 80, or electronic storage 130 may be provided integrally with one or more other components of system 80 (e.g., processor 110).

User interface 120 of system 80 in FIG. 8 is configured to provide an interface between system 80 and a user (e.g., a user 108, a caregiver, a therapy decision-maker, etc.) through which the user can provide information to and receive information from system 80. This enables data, results, and/or instructions and any other communicable items, collectively referred to as "information," to be communicated between the user and system 80. An example of information that may be conveyed to user 108 is an indication of the volume and/or intensity of the sound signals produced by playback component 112. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 80 from removable storage (e.g., a smart card, a flash drive, a removable disk, etc.) that enables the user(s) to customize system 80. Other exemplary input devices and techniques adapted for use with system 80 as user interface 120 include, but are not limited to, an RS-232 port, RF link, an IR link, modem (telephone, cable, Ethernet, internet or other). In short, any technique for communicating information with system 80 is contemplated as user interface 120.

Figure 9:
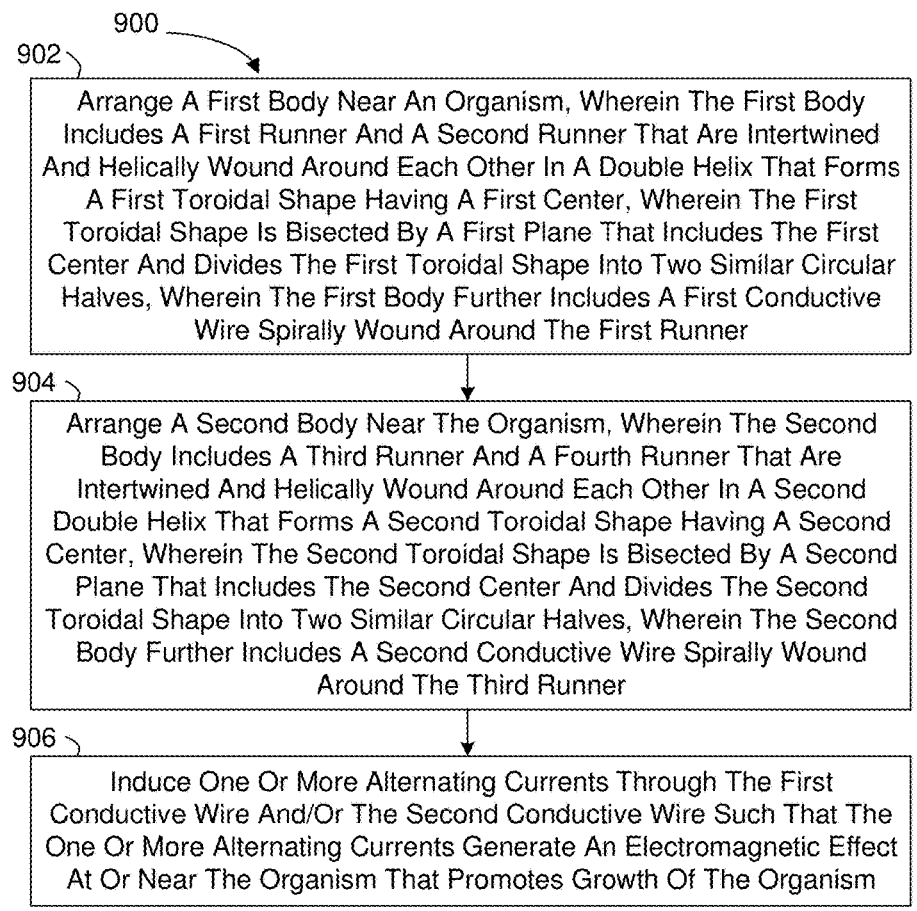
FIG. 9 illustrates a method for providing electromagnetic effects and/or promoting growth of one or more organisms, according to one or more implementations.

FIG. 9 illustrates a method 900 for providing electromagnetic effects. The operations of method 900 presented below are intended to be illustrative. In certain implementations, method 900 may be accomplished with one or more additional operations not described, and/or without one or more of the operations discussed. Additionally, the order in which the operations of method 900 are illustrated in FIG. 9 and described below is not intended to be limiting.

In certain implementations, method 900 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of method 900.

Regarding method 900, at an operation 902, a first body is arranged at or near an organism. The first body includes a first runner and a second runner that are intertwined and helically wound around each other in a double helix that forms a first toroidal shape having a first center. The first toroidal shape is bisected by a first plane that includes the first center and divides the first toroidal shape into two similar circular halves. The first body further includes a first conductive wire spirally wound around the first runner. In some embodiments, operation 902 is performed by a body the same as or similar to body 40a (shown in FIG. 8 and described herein).

At an operation 904, a second body is arranged near the organism. The second body includes a third runner and a fourth runner that are intertwined and helically wound around each other in a second double helix that forms a second toroidal shape having a second center. The second toroidal shape is bisected by a second plane that includes the second center and divides the second toroidal shape into two similar circular halves. The second body further includes a second conductive wire spirally wound around the third runner. In some embodiments, operation 904 is performed by a body the same as or similar to body 40b (shown in FIG. 8 and described herein). In some embodiments, operation 904 and a second body may be omitted.

At an operation 906, one or more alternating currents are induced through the first conductive wire and/or the second conductive wire such that the one or more alternating currents generate an electromagnetic effect at or near the organism that promotes growth of the organism. In some embodiments, operation 906 is performed by a current source the same as or similar to current source 12a and/or current source 12b (shown in FIG. 8 and described herein). The bodies are arranged such that the first plane is parallel to the second plane. The bodies are arranged such that the organism is positioned between the bodies.

Although the invention has been described in detail for the purpose of illustration based on what is currently considered to be the most practical and preferred implementations, it is to be understood that such detail is solely for that purpose and that the invention is not limited to the disclosed implementations, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system comprising:
   a first body including:
      a first runner and a second runner that are intertwined and helically wound around each other in a double helix that forms a first toroidal shape comprising a first center, wherein the first toroidal shape is bisected by a first plane that includes the first center and divides the first toroidal shape into two circular halves; and a first conductive wire spirally wound around the first runner;
   a second body including:
      a third runner and a fourth runner that are intertwined and helically wound around each other in a second double helix that forms a second toroidal shape comprising a second center, wherein the second toroidal shape is bisected by a second plane that includes the second center and divides the second toroidal shape into two circular halves; and a second conductive wire spirally wound around the third runner; and one or more current sources that provide one or more alternating currents to the first conductive wire and the second conductive wire, wherein the first body and the second body are arranged such that the first plane is parallel to the second plane, wherein the first body and the second body are configured to be arranged such that an organism is positioned between the first body and the second body, and wherein the system is configured to generate an electromagnetic effect responsive to the one or more alternating currents being provided such that the electromagnetic effect promotes growth of the organism.

2. The system of claim 1, wherein the first body and the second body are further arranged such that a line through the first center and the second center is perpendicular to the first plane and to the second plane.

3. The system of claim 1, wherein the first and second toroidal shape comprise at least two complete revolutions.

4. The system of claim 1, wherein the first conductive wire is arranged at a fixed distance from the first runner, and wherein the second conductive wire is arranged at a second fixed distance from the second runner.

5. The system of claim 1, wherein the first runner comprises a first surface, wherein the second runner comprises a second surface, wherein the first conductive wire is arranged at a fixed distance from the first surface of the first runner, and wherein the second conductive wire is arranged at a second fixed distance from the second surface of the second runner.

6. The system of claim 1, wherein the first conductive wire is wound around the first runner in a helical shape that comprises an axis, wherein the axis coincides with the first runner.

7. The system of claim 1, wherein the first conductive wire is a twisted wire, and wherein the second conductive wire is a second twisted wire.

8. The system of claim 1, wherein the one or more current sources are further configured such that the one or more alternating currents include a first alternating current that comprises a first carrier wave modulated by a first acoustic signal, wherein the first carrier wave comprises a higher frequency than the first acoustic signal.

9. The system of claim 1, wherein the double helix of the first body comprises a diameter between 4 inches and 10 feet.

10. The system of claim 1, wherein the first body and the second body are arranged between 4 inches and 10 feet apart.

11. The system of claim 1, wherein the first body and the second body are arranged between 10 feet and 10000 feet apart.

12. The system of claim 1, wherein the one or more alternating currents include a first alternating current that comprises a first carrier wave with a frequency, and wherein the frequency of the first carrier wave is between 1 MHz and 1 GHz.

13. The system of claim 1, wherein the electromagnetic effect includes an electromagnetic field.

14. The system of claim 1, wherein the promotion of growth includes one or more of an increased growth rate, an increased maximum growth level, an increased maximum yield, and an increased feed conversion rate.

15. The system of claim 1, further comprising: one or more physical processors configured via computer-readable instructions to: obtain information that includes one or more digital audio files; process the obtained information and generate a processed signal based on the obtained information, and produce sound signals based on the processed signal, wherein the one or more alternating currents are dynamically controlled to correspond to the produced sound signals such that one or more frequencies of the one or more alternating currents correspond to one or more frequencies of the produced sound signals.

16. A method for providing electromagnetic effects, the method comprising:

arranging a first body near an organism, wherein the first body includes a first runner and a second runner that are intertwined and helically wound around each other in a double helix that forms a first toroidal shape comprising a first center, wherein the first toroidal shape is bisected by a first plane that includes the first center and divides the first toroidal shape into two circular halves, wherein the first body further includes a first conductive wire spirally wound around the first runner;

arranging a second body near the organism, wherein the second body includes a third runner and a fourth runner that are intertwined and helically wound around each other in a second double helix that forms a second toroidal shape comprising a second center, wherein the second toroidal shape is bisected by a second plane that includes the second center and divides the second toroidal shape into two circular halves, wherein the second body further includes a second conductive wire spirally wound around the third runner; and inducing one or more alternating currents through the first conductive wire and the second conductive wire such that the one or more alternating currents generate an electromagnetic effect at or near the organism that promotes growth of the organism;

wherein the first body and the second body are arranged such that the first plane is parallel to the second plane, wherein the first body and the second body are arranged such that the organism is positioned between the first body and the second body.

17. The method of claim 16, wherein arranging the first body and the second body is accomplished such that a line through the first center and the second center is perpendicular to the first plane and to the second plane.

18. The method of claim 16, wherein arranging the first body includes arranging the first toroidal shape in at least two complete revolutions, and wherein arranging the second body includes arranging the second toroidal shape in at least two complete revolutions.

19. The method of claim 16, wherein arranging the first body includes arranging the first conductive wire at a fixed distance from the first runner, and wherein arranging the second body includes arranging the second conductive wire at a second fixed distance from the second runner.

20. The method of claim 16, wherein the first runner comprises a first surface, wherein the second runner comprises a second surface, wherein arranging the first body includes arranging the first conductive wire at a fixed distance from the first surface of the first runner, and wherein arranging the second body includes arranging the second conductive wire at a second fixed distance from the second surface of the second runner.

21. The method of claim 16, wherein arranging the first body includes winding the first conductive wire around the first runner in a helical shape that comprises an axis, wherein the axis coincides with the first runner.

22. The method of claim 16, wherein the first conductive wire is a twisted wire, and wherein the second conductive wire is a second twisted wire.

23. The method of claim 16, wherein inducing the one or more alternating currents includes inducing a first alternating current that comprises a first carrier wave modulated by a first acoustic signal, wherein the first carrier wave comprises a higher frequency than the first acoustic signal.

24. The method of claim 16, wherein arranging the first body includes arranging the double helix that comprises a diameter between 4 inches and 10 feet.

25. The method of claim 16, wherein arranging the first body and the second body includes arranging the first body and the second body between 4 inches and 10 feet apart.

26. The method of claim 16, wherein arranging the first body and the second body includes arranging the first body and the second body between 10 feet and 10000 feet apart.

27. The method of claim 16, wherein inducing the one or more alternating currents includes modulating a first carrier wave by a first acoustic signal, wherein the first carrier wave comprises a frequency, and wherein the frequency of the first carrier wave is between 1 MHz and 1 GHz.

28. The method of claim 16, wherein inducing the one or more alternating currents includes generating an electromagnetic field.

29. The method of claim 16, wherein generating the electromagnetic effect includes promoting growth of the organism by one or more of an increased growth rate, an increased maximum growth level, an increased maximum yield, and an increased feed conversion rate.

30. The method of claim 16, further comprising:
obtaining information that includes one or more digital audio files;
processing the obtained information and generate a processed signal based on the obtained information, and
producing sound signals based on the processed signal,
wherein inducing the one or more alternating currents includes dynamically controlling the one or more alternating currents to correspond to the produced sound signals such that one or more frequencies of the one or more alternating currents correspond to one or more frequencies of the produced sound signals.

* * * * *